United States Patent
Thaysen

(10) Patent No.: US 7,284,452 B2
(45) Date of Patent: Oct. 23, 2007

(54) CANTILEVER SENSOR USING BOTH THE LONGITUDINAL AND THE TRANSVERSAL PIEZORESISTIVE COEFFICIENTS

(75) Inventor: Jacob Thaysen, Copenhagen (DK)

(73) Assignee: Nanonord A/S, Aalborg (DK)

( * ) Notice: Subject to any disclaimer, the term of this patent is extended or adjusted under 35 U.S.C. 154(b) by 208 days.

(21) Appl. No.: 10/539,820

(22) PCT Filed: Dec. 20, 2003

(86) PCT No.: PCT/DK03/00918

§ 371 (c)(1),
(2), (4) Date: Jun. 20, 2005

(87) PCT Pub. No.: WO2004/059306

PCT Pub. Date: Jul. 15, 2004

(65) Prior Publication Data

US 2006/0060003 A1    Mar. 23, 2006

Related U.S. Application Data

(60) Provisional application No. 60/444,676, filed on Feb. 4, 2003.

(30) Foreign Application Priority Data

Dec. 27, 2002 (DK) .............................. 2002 02016
Jan. 21, 2003 (DK) .............................. 2003 00068

(51) Int. Cl.
*G01L 1/04* (2006.01)
(52) U.S. Cl. ................................................. 73/862.639
(58) Field of Classification Search ............ 73/862.639
See application file for complete search history.

(56) References Cited

U.S. PATENT DOCUMENTS 4,311,980 A    1/1982 Prudenziati (Continued)

FOREIGN PATENT DOCUMENTS

WO    WO99/38007    7/1999

(Continued)

OTHER PUBLICATIONS

H. Chen et al., "A Piezoresistive Accelerometer with a Novel Vertical Beam Structure", Sensors and Actuators, vol. 63, pp. 19-25, 1997.

(Continued)

*Primary Examiner*—Max Noori
(74) *Attorney, Agent, or Firm*—Finnegan, Henderson, Farabow, Garrett & Dunner, LLP

(57) ABSTRACT

The present invention relates to a sensor comprising least one sensor unit e.g. a cantilever. The sensor unit comprises a capture surface area and a piezoresistive detection system, for direct detection of stress change of the sensor unit when applying an electrical field over the piezoresistive element. The piezoresistive element has a longitudinal direction in the current direction and a transverse direction perpendicular there to. The longitudinal direction and the transverse direction each has a stress composant and a current composant. The piezoresistive element is of an anisotropic material, and is arranged so that the numerically value of the sum of the longitudinal piezoresistive coefficient $\pi_l$ and the transverse piezoresistive coefficient $\pi_t$ along at least 25% of the length, of the piezoresistive element is at least $10^{-10}$ $Pa^{-1} \times P$, such as $2 \times 10^{-10}$ $Pa^{-1} \times P$, such as $3 \times 10^{-10}$ $Pa^{-1} \times P$, such as $4 \times 10^{-10}$ $Pa^{-1} \times P$, wherein P is the piezoresistance factor, and wherein the piezoresistive coefficients $\pi_l$ and $\pi_t$ are determined as composants in the coordinate system used to determine the longitudinal direction.

27 Claims, 4 Drawing Sheets

U.S. PATENT DOCUMENTS

| | | | |
|---|---|---|---|
| 5,275,055 A | | 1/1994 | Zook et al. |
| 5,563,341 A | * | 10/1996 | Fenner et al. ............ 73/335.11 |
| 5,659,138 A | * | 8/1997 | Iwata et al. ............. 73/514.33 |

FOREIGN PATENT DOCUMENTS

| | | |
|---|---|---|
| WO | WO00/14539 | 3/2000 |
| WO | WO00/66266 | 11/2000 |
| WO | WO03/044530 A1 | 5/2003 |
| WO | WO03/062135 A1 | 7/2003 |
| WO | WO03/067248 A1 | 8/2003 |
| WO | WO03/071258 A1 | 8/2003 |
| WO | WO03/104794 A1 | 12/2003 |

OTHER PUBLICATIONS

Marc Madou: "Fundamentals of microfabrication" 1997, ISBN: 0-8493-9451-1, pp. 160-163.

Toriyama T et al: "Single crystal silicon nano-wire piezoresistors for mechanical sensors"; Journal of Microelectromechanical Systems, IEEE, vol. 11, No. 5, pp. 605-611, Oct. 2002.

Harley J. A et al.: "1/f noise considerations for the design and process optimization of piezoresistive cantilevers"; Journal of Microelectromechanical Systems IEEE, vol. 9, No. 2, pp. 226-235, Jun. 2000.

Jaeger R C et al.: "Off-axis sensor rosettes for measurement of the piezoresistive coeeficients of silicon"; IEEE Transactions on Components, Hyrids, and manufacturing Technology, vol. 16, No. 8, pp. 925-931, Dec. 1993.

Jacob Thaysen "Cantilever for Bio-Chemical Sensing Integrated in a Microliquid Handling System". Ph.D Thesis, Mikroelektronik Centret, Sep. 2001.

Stanley W. Polchlopek et al , "Properties of Nitrogen-Implanted SOI Substrates", IEEE Transaction on electron devices. vol. 40.No. 2, Feb. 1993.

Thaysen J. et al., "Atomic Force Microscopy probe with piezoresistive read-out and high symmetrical Wheatstone bridge arrangement" Proceedings of Transducers '99, 1252-1855, pp. 47-53, (1999).

Thaysen et al. "Cantilever-based bio-chemical sensor integrated in a microliquid handling system".

Technical Digest, 14$^{th}$ IEEE. International conference on micro electro mechanical systems. ISBN: 0-7803-5998-4, . 2001.

Samuel Kassegne et al: "Design Issues in SOI-Based High-Sensitivity Piezoresistive Cantilever Devices"; Nanogen Inc.

S. M. Sze, "Classification and terminology of sensors", Semiconductor Sensors, ISBN 0-471-54609-7, John Wiley & Sons Inc., pp. 160-169, 1994.

Y Kanda, "A graphical representation of the piezoresistance coefficients in silicon" IEEE Trans. Electron Devices, vol. ED-29, pp. 64-70, Jan. 1982.

* cited by examiner

A

B

CANTILEVER SENSOR USING BOTH THE LONGITUDINAL AND THE TRANSVERSAL PIEZORESISTIVE COEFFICIENTS

This application is a national phase entry of international application number PCT/DK2003/000918, filed Dec. 20, 2003, which claims the benefit of priority to Danish application number 2002 02016, filed Dec. 27, 2002, Danish application number 2003 00068, filed Jan. 21, 2003, and U.S. Provisional Application 60/444,676, filed Feb. 4, 2003.

FIELD OF THE INVENTION

The present invention relates to a sensor comprising one or more sensor units, wherein each sensor units comprises a capture surface area and a piezoresistive detection system, for direct detection of stress change of the sensor unit. One type—the most commonly used type of sensor unit—is a cantilever.

The invention also relates to a method of producing such sensor.

BACKGROUND OF THE INVENTION

In the art of detecting components in fluids, cantilever based sensors with integrated piezoresistors are used as very sensitive mechanical stress sensors. As described in e.g. WO 0066266 and WO 9938007, micro cantilevers can be used for detection of molecular interaction. At least one surface of the cantilever is coated with a capture layer, which capture layer reacts with a target molecule of interest. If the cantilever is exposed to a sample in which the target molecule is present, the target molecule will react with the capture molecule on the cantilever surface and a surface stress change will be generated.

Due to the surface stress change of the cantilever, a mechanical compression, stretch or decompression is applied to the cantilever and thereby also to the piezoresistor, and thereby the resistivity of the piezoresistor changes its value. The mechanical compression or decompression may result in a deflection and/or a stretch and/or a contraction. By measuring the change in resistance, it can be determined whether the target molecule is present in the sample or not, and if so it may also be possibly to detect the concentration of the target molecule.

Cantilever-based sensors with integrated piezoresistive read-out are described by Thaysen, Ph.D. Thesis, "Cantilever for Bio-Chemical Sensing Integrated in a Microliquid Handling System", September 2001, Microelektronik Centeret, Technical University of Denmark. Hereby the stress changes on the cantilever sensors can be measured directly by the piezoresistor. Moreover, integrated read-out greatly facilitates operation in solutions since the refractive indices of the fluids do not influence the detection as it will using optical read-out. Each sensor may have a built-in reference cantilever, which makes it possible to subtract background drift directly in the measurement. Furthermore, by functionalizing the reference cantilever with a "dummy" molecule, non-specific binding events occuring on both the measurement and reference cantilever will be cancelled out in the differential measurement.

The two cantilevers may be connected in a Whetstone bridge, and the stress change on the measurement cantilever is detected as the output voltage from the Whetstone Reference is also made to "Design issues in SOI-based high-sensitivity piezoresistive cantilever devices" by Kassegne et al. Proceedings of the SPIE Conference on Smart Structures and Materials, San Diego, Calif., Mar. 17-21 2002.

The objective of the present invention is to provide a sensor comprising one or more sensor units with a capture surface, which sensor can be used for detection of the presence of a target in a fluid, such as a chemical component in a liquid or a gas e.g. for detecting an explosive, a drug, a biocomponent or other components in a fluid with an improved signal or signal/noise ratio than according to the prior art cantilevered fluid sensors.

This and other objectives as it will be clear from the following description, has been solved by the invention as it is defined in the claims.

DISCLOSURE OF THE INVENTION

The sensor of the invention comprises one or more sensor units. The shape and size of the sensor and the size, shape and the number of sensor units as well as its wiring, may e.g. be as disclosed in any one of the patent applications WO 0066266, DK PA 2001 01724 DK PA 2002 00283, DK PA 2002 00125 and DK PA 2002 00195, which with respect to the disclosure concerning structure (shape and size of the sensor and the size, shape and the number of sensor units as well as its wiring) are hereby incorporated by reference.

In the following the sensor is described with one sensor unit, only, but it should be understood that the sensor unit may have several sensor units, such as up to 300, e.g. up to 100.

The sensor unit may in principle have any cantileverlike shape e.g. as the cantilevers described in DK PA 2002 00125. The term 'cantilever shape' is defined as a sheet formed unit linked to a substrate (or two substrates) along one or two opposite edge lines. The term 'cantilever shape' thus also includes a bridge, as well as a traditional rectangular, triangular or leaf shaped cantilever.

In one embodiment, the sensor unit shaped as a cantilever extending in a length between two endings and linked in both of its endings to form a cantilevered bridge.

In another embodiment, the cantilever is a traditional rectangular or leaf shaped cantilever linked to one substrate only. In the following this type of cantilevers are referred to as cantilevers with a free end.

The sensor unit comprises two major surfaces, wherein one or both of these totally or partly may constitute a capture surface.

In one embodiment the sensor unit is a flexible sheet-formed unit having an average thickness which is thinner than both its average length and its average width, said sensor unit preferably have a thickness of between 0.05 and 5 µm, such as in the interval of 0.1 µm to 4 µm, such as in the interval of 0.2 µm to 1 µm.

In one embodiment the sensor unit is a flexible sheet-formed unit having an average thickness which is at least 5 times, preferably at least 50 times less than its average width and average length.

The sensor unit has a capture surface e.g. in the form of a capture coating. The capture coating may e.g. be as described in any one of the applications DK PA 2002 00283 and DK PA 2002 00125 or in U.S. Pat. No. 6,289,717, WO 0133226 or WO 0014539, which with respect to the disclosure concerning the capture surface are hereby incorporated by reference.

In one embodiment of the sensor according to the invention, the capture surface is a surface of a capture coating comprising a capture layer, wherein said capture layer is a layer comprising a detection ligand, said detection ligand may be a member of a specific binding pair or it may be adapted for capturing a group of components or even for unspecific binding. The detection ligand is preferably selected from the group consisting of RNA oligos, DNA oligos, PNA oligos, proteins, enzymes, receptors, peptides, hormones, blood components, antigen and antibodies.

In one embodiment of the sensor according to the invention, the capture surface is a surface of a capture coating comprising a capture layer, of polymer, hydrogel or metal/metal containing component e.g. comprising a functional group selected from the group consisting of carboxylic acids, sulfonic acid derivatives, esters, acid halides, acid hydrazides, semicarbazides, thiosemicarbaxides, nitriles, aldehydes, ketones, alcohols, thiols, disulphides, amines, hydrazines, ethers, epoxides, sulphides, halides and derivatives thereof.

The capture coating could in principle have any thickness. If the capture coating is very thick the sensitivity may be reduced due to stiffness of sensor unit. A desired thickness could e.g. be from molecular thickness to 2000 nm, such as up to, 2, 5, 10 or 50 molecule layers, or e.g. between 0.5 nm and 1000 nm, such as between 1 and 500 nm, such as between 10 and 200 nm.

In one embodiment both or a part of both of the two major sides of the cantilever comprise a capture surface. The capture surfaces may be identical or they may differ from each other e.g. with respect to size of area covered, type of capture molecules and/or concentrations thereof. In one embodiment the capture surface on one major side of a cantilever is essentially identical,—both with respect to size of area covered, type of capture molecules and concentrations—to the capture surface on the other one of the two opposite major surfaces of the cantilever. In this situation the stress generated on the cantilever when subjected to a fluid containing the target molecules, will be equal on both sides of the cantilever, and consequently, if the cantilever is of the type with a free end, the cantilever will not bend, but only stretch or contract.

In practice it is very cumbersome to produce a cantilever with two opposite major sides with identical capture surfaces. Thus, the cantilever will in most situations, even when carrying capture surfaces on both of each major sides, be subjected to at least a slightly bending due to different stress generated on the opposite major sides of the cantilever.

The sensor unit comprises a piezoresistive element with a pair of wires for applying an electrical field over the piezoresistive element. The distance between the wires along the piezoresistive element is defined as the length of the piezoresistive element. This means in practice that the length of the piezoresistive element is the length that the current has to travel through the piezoresistive element. In one embodiment the length of the piezoresistive element is thus defined as the length the current has to travel.

The piezoresistor may have any shape e.g. as described in any one of the patent applications WO 0066266, DK PA 01724 DK PA 2002 00283, DK PA 2002 00125 and DK PA 2002 00195. The piezoresistive element may e.g. be, latter shaped, meander shaped, U shaped or V shaped.

In practice it is most simple to either provide the piezoresistive element as a straight element when the cantilever is linked to be a bridge or provide the piezoresistive element as a horse shoe shape when the cantilever has a free end.

The piezoresistive element has a longitudinal direction and a transverse direction along the length of the piezoresistive element when an electrical field is applied over the piezoresistive element and the piezoresistive element is subjected to a stress. The longitudinal direction and the transverse direction may vary along the length of the piezoresistive element if the piezoresistive element is not straight.

The coordinate system may in principle be aligned as desired provided that the longitudinal direction is defined as a direction which is one of the x, y or z axis of a coordinate system and wherein there is a stress composant and a current composant. The resulting numerically value of the sum of the longitudinal piezoresistive coefficient $\pi_l$ and the transverse piezoresistive coefficient $\pi_t$ can thereby be detected.

In one embodiment for simple calculation the coordinate system should preferably be aligned so that only one direction for a given point along the length of the piezoresistive element qualifies as a longitudinal direction.

In one embodiment the coordinate system is aligned to the crystal axis.

The most simple calculation is provided when the coordinate system is aligned so that the direction of the current through the piezoresistive element is the longitudinal direction. This system is used below in the examples.

The transverse direction is perpendicular to the longitudinal direction. In one embodiment the transverse direction also has a stress composant.

If we consider the surface stress of a local point of the sensor piezoresistive element, the sensor will in principle bend a a cup in all directions if no other forces are involved. The piezoresistive element is thus stressed in all directions in this point, and this stress is divided into two stress composant a longitudinal and a transversal. For simple calculation the longitudinal stress composant is in the direction of the current.

Further information concerning determination of longitudinal and transversal direction in a silicon piezoresistive element can be found in "Classification and terminology of sensors, S. M. SZE, Semiconductor Sensors, ISBN 0-471-54609-7, 1994, John Wiley & Sons Inc. pages 160-169 which is hereby incorporated by reference.

In one embodiment, the piezoresistive element is a straight element, the piezoresistive element has only one longitudinal and transverse directions along its length. In another embodiment, the piezoresistive element is shaped as a horse shoe, the piezoresistive element has two longitudinal and transverse directions along its length.

The piezoresistive element is of an anisotropic material, is being arranged so that the numerically value of the sum of the longitudinal piezoresistive coefficient $\pi_l$ and the transverse piezoresistive coefficient $\pi_t$ along at least 25% of the length, such as at least along 50% of the length such as at least along 80% of the length, such as at least along 90% of the length, such as at least along 95% of the length of the piezoresistive element being at least $10^{-10}$ Pa$^{-1}$×P, such as $2\times10^{-10}$ Pa$^{-1}$×P, such as $3\times10^{-1}$ Pa$^{-1}$×P, such as $4\times10^{-10}$ Pa$^{-1}$×P, wherein P is the piezoresistance factor, and wherein the piezoresistive coefficients $\pi_l$ and $\pi_t$ are determined as composants in the coordinate system used to determine the longitudinal direction.

In one embodiment the numerically value of the sum of the longitudinal piezoresistive coefficient $\pi_l$ and the transverse piezoresistive coefficient $\pi_t$ along the whole of its length is at least $10^{-10}$ Pa$^{-1}$×P, such as $2\times10^{-10}$ Pa$^{-1}$×P, such as $3\times10^{-10}$ Pa$^{-1}$×P, such as $4\times10^{-10}$ Pa$^{-1}$×P.

The piezoresistance factor P is depending on the doping level. P is between 0 and 1. For single crystalline silicon P is about 1 at a doping level around $10^{18}$. Further information concerning the P factor and the determination thereof can be found in "1/F Noise Considerations for the Design and Process Optimization of Piezoresistive Cantilevers" by Jonah A. Harley and Thomas W. Kenny. Journal of microelectromechanical systems. Vol, 9, No. 2, pp 226-235. June 2000. Reference is in particular made to FIG. 7. Reference is also made to Y. Kanda. "A graphical representation of the piezoresistance coefficients in silicon" IEEE Trans. Electron Devices, Vol. ED-29, pp 64-70, January 1982.

A piezoresistive effect in a material indicates the fractional change in bulk resistivity induced by a small mechanical stress applied to the material. Single crystalline silicon has a high piezoresistivity, and combined with its excellent mechanical and electronic properties, it makes it a useful material for the conversion of a mechanical signal into an electrical signal.

The piezoresistive element may therefore preferably be of doped single crystalline silicon. In one embodiment the piezoresistive element is of single crystalline silicon doped with $10^{16}$ ions/cm$^3$ or more, such as $10^{17}$ ions/cm$^3$ or more, such as $10^{18}$ ions/cm$^3$ or more, such as $10^{19}$ ions/cm$^3$ or more, such as $10^{20}$ ions/cm$^3$ or more.

In one embodiment the piezoresistive element is of single crystalline silicon doped with $10^{20}$ ions/cm$^3$ or less, such as $10^{19}$ ions/cm$^3$ or less, such as $10^{18}$ ions/cm$^3$ or less, such as $10^{17}$ ions/cm$^3$ or less.

The higher level of doping ions the lower is the amount of noise, however simultaneously the signal will also be reduced accordingly. The temperature may also influence the noise as well as the signal, and accordingly the effect of temperature should also be considered. The optimal doping level can easily be found by the skilled person based on the present teaching. Optimal doping level will be in the interval $10^{16}$ ions/cm$^3$–$10^{21}$ ions/cm$^3$.

In one embodiment the surplus or shortage of electrons due to the doping is within the interval $10^{16}$ ions/cm$^3$–$10^{21}$ ions/cm$^3$.

The doping ions may in principle be any type of ions usable for doping silicon or mixtures of ions. In one embodiment, when n-type and p-type ions are mixed, it is desired that the piezoresistive element comprise at least $10^{16}$ ions/cm$^3$, such as $10^{17}$ ions/cm$^3$ or more, such as $10^{18}$ ions/cm3 or more, such as $10^{19}$ ions/cm$^3$ or more, such as $10^{20}$ ions/cm$^3$ or more, more of one of the types than of the other one of the types.

In one embodiment, the piezoresistive element being of single crystalline silicon doped with one or more of the ions boron ion, phosphorous ion, arsenic ion.

In one embodiment the piezoresistive element is n-type single crystalline silicon. The n-type single crystalline silicon may e.g. be orientated along the <110> direction of silicon. In another embodiment the n-type silicon piezoresistive element is orientated along the <100> direction of silicon.

The thickness of the piezoresistive element may e.g. be at least 10 nm, such as in the interval of 10 nm to 500 nm, such as in the interval of 50 nm to 300 nm, such as in the interval of 100 nm to 200 nm.

As mentioned, the sensor unit also comprise a pair of wires for applying an electrical field over the piezoresistor, e.g. as described in any one of the patent applications WO 0066266, DK PA 01724 DK PA 2002 00283, DK PA 2002 00125 and DK PA 2002 00195.

In one embodiment of the sensor according to the invention, where the sensor unit comprises two major surfaces, and at least a part of one or both of the major surfaces constitutes the capture surface, the piezoresistive element has a neutral plan distance of 50 nm or less, such as 100 nm or less, such as 200 nm or less, such as 400 nm or less, such as 1 μm or less, such as 3 μm or less. The neutral plan distance is measured as the shortest distance between the middle plan of the piezoresistive element and the neutral plan. The middle plan of the piezoresistive element is defined as the middle plan through the piezoresistive element which is parallel to the neutral plan. The neutral plan is defined as the plan along which the sum of the compressive and tensile stress acting on the piezoresistive element is as close to zero as possible.

In one embodiment, the sensor unit further comprise a current shield, e.g. as described in DK PA 2002 00884 DK filed Jun. 7, 2002.

The shield may have a diffusion barrier which is sufficient to prevent the diffusion of an electrolyte to leak current from the piezoresistor when an acidic liquid at a pH of 4 is held in contact with the capture surface for a period of 1 or even 2 minutes or even 10 minutes under standard conditions.

In one embodiment the shield is of a non-conducting material selected from the group consisting of nitrides, such as silicon nitride and tantalum nitride, non-conducting polymers, such as octafunctional epoxidized novalac, metal oxides, such as aluminium oxide, ceramics, diamond films, silicon carbide, tantalum oxide, silicon, glass, mixtures and combinations thereof.

In one embodiment the piezoresistive element is of doped n-type single crystalline silicon and the shield is of doped p-type single crystalline silicon, preferably a p-type single crystalline silicon with a doping level which is lower than the doping level of the n-type single crystalline silicon piezoresistive element. The p-type single crystalline silicon shield may e.g. have a doping ion concentration of $10^{20}$ cm$^{-3}$ or less, such as a doping ion concentration of $10^{19}$ cm$^{-3}$ or less, such as a doping ion concentration of $10^{18}$ cm$^{-3}$ or less, such as a doping ion concentration of $10^{17}$ cm$^{-3}$ or less, such as a doping ion concentration of $10^{16}$ cm$^{-3}$ or less, such as a doping ion concentration of $10^{15}$ cm$^{-3}$ or less.

In one embodiment the sensor unit comprise a bottom shield layer and a top shield layer, and an edge shield layer. The bottom shield layer, top shield layer and edge shield layer constitute the shield.

A sensor wherein the sensor units comprise a shield may preferably be used for detection of a substance in a liquid, such as an aqueous liquid.

The sensor may preferably comprise one or more fluid chambers (e.g. liquid chambers). In one embodiment the one or more sensor units partly or totally protrudes into the fluid chamber(s) so that a fluid applied in the chamber is capable of coming into contact with part of the surface of the sensor unit(s).

The fluid chamber or chambers may e.g. be in the form of interaction chamber(s), preferably comprising a channel for feeding a fluid such as a liquid into the interaction chamber(s).

In one embodiment at least 50%, more preferably substantially all of the capture surface of the sensor unit or units is positioned inside the fluid interaction chamber(s).

The sensor may e.g. be prepared as described in DK PA 2002 00884 DK with the difference that the doping may be an n-type doping and that the single crystalline silicon piezoresistive element is arranged so that the numerically value of the sum of the longitudinal piezoresistive coefficient $\pi_l$ and the transverse piezoresistive coefficient $\pi_t$ along the major length, such as at least along 25% of the length, such as at least along 50% of the length, such as at least along 60% of the length, such as at least along 80% of the length, such as at least along 90% of the length, such as at least along 95% of the length of the piezoresistive element being at least $10^{-10}$ Pa$^{-1}$×P, such as $2\times10^{-10}$ Pa$^{-1}$×P, such as $3\times0\ 10^{-10}$ Pa$^{-1}$×P, such as $4\times10^{-10}$ Pa$^{-1}$×P.

FIGURES AND EXAMPLES

Embodiments of the invention will be described further with reference to the figures and examples.

Figure 3:
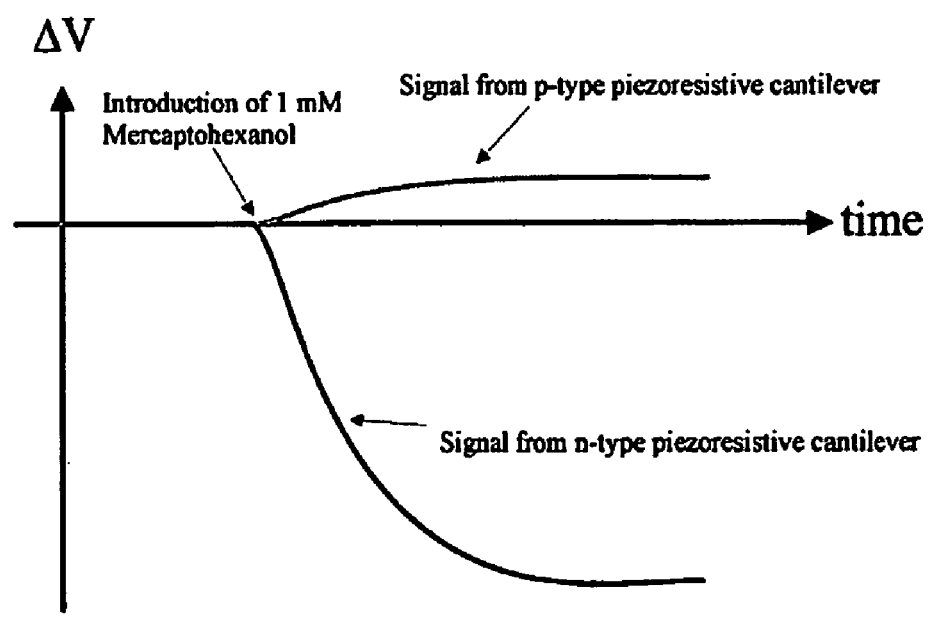

FIG. 3, shows a change in signal due to immobilization of 1 mM Mercaptohexanol for respectively a sensor unit with an n-type piezoresistive element and a sensor unit with a p-type piezoresistive element. It can be seen that the signal from the n-type cantilever is about a factor of 8 larger than the signal obtained from the p-type piezoresistive cantilever. Note that the change in output voltage for the n-type piezoresistive cantilever is negative compared to the p-type piezoresistive cantilever.

Figure 4:

FIG. 4 is a schematic illustration of a cantilever.

Figure 5:
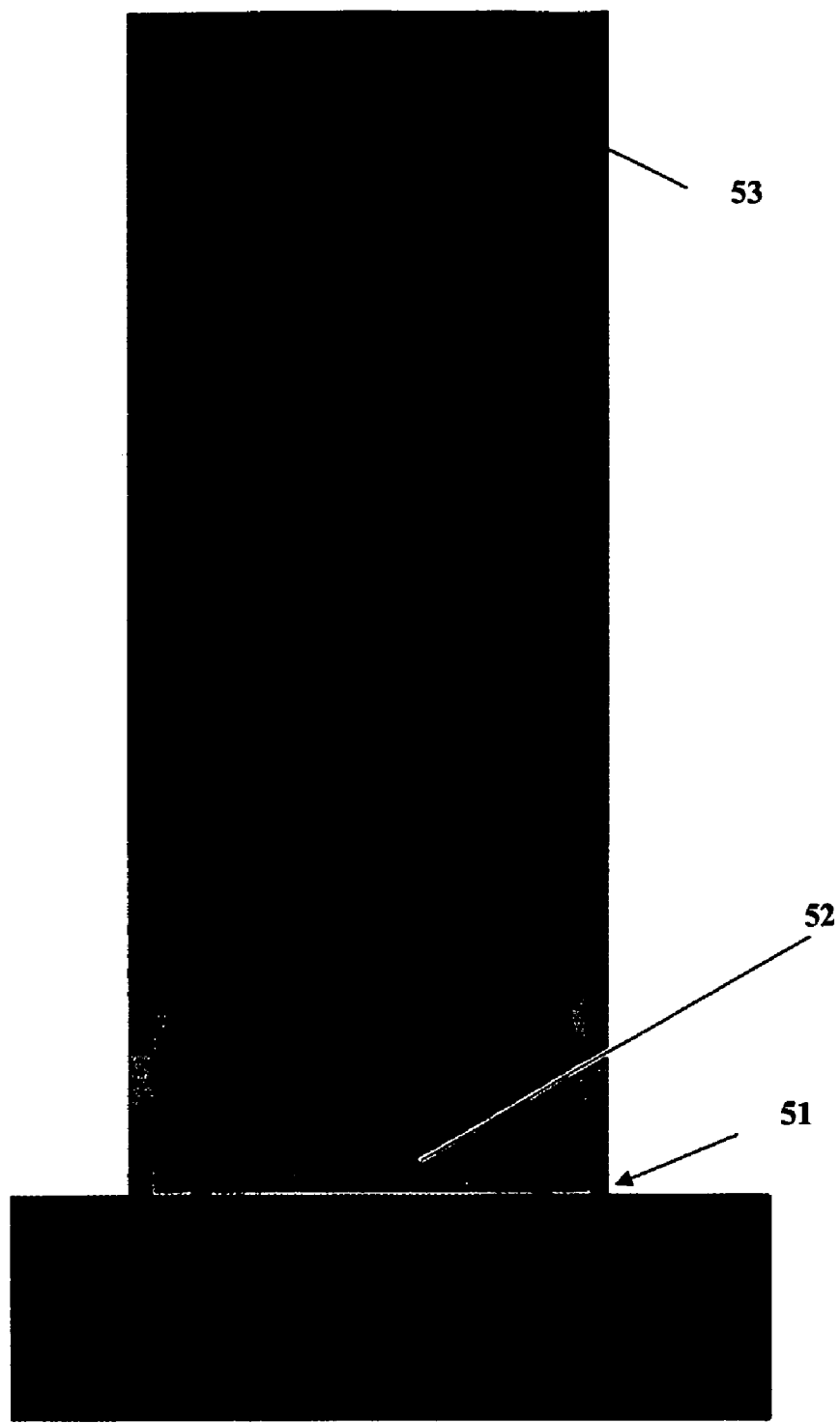

FIG. 5 shows a cantilever with a stressed surface.

The piezoresistivity in single crystalline silicon is anisotropic and therefore the sensitivity is also dependent on the piezoresistor orientation with respect to the silicon crystalline. According to the invention it has been found that the contribution to the relative resistance changes from stress generated on a cantilever surface is given by:

$$\frac{\Delta R}{R} = \sigma_l \pi_l + \sigma_t \pi_t \quad (1)$$

where $\sigma_l$ and $\sigma_t$ is the longitudinal and transverse stress respectively, while $\pi_l$ and $\pi_t$ indicates the piezoresistive coefficients. For p-type/n-type silicon wafer with (100) plane at the surface of the wafer the piezoresistive coefficients at room temperature (in $10^{-11}$ Pa$^{-1}$) and doping level about $10^{18}$ cm$^{-3}$ (p is approximately 1) is given in table 1.

TABLE 1

| | Direction | $\pi_{11}$ | $\pi_{12}$ | $\pi_{44}$ | $\pi_t$ | $\pi_l$ |
|---|---|---|---|---|---|---|
| p-Si | <100> | | | | 0 | 0 |
| | <110> | 6.6 | −1.1 | 138.1 | −66 | 72 |
| n-Si | <100> | | | | 53 | −102 |
| | <110> | −102.2 | 53.4 | −13.6 | −18 | −31 |

The longitudinal piezoresistive coefficient in the <110> direction is determined as $\pi_l = 1/2(\pi_{11} + \pi_{12} + \pi_{44})$, and the corresponding transverse coefficient is $\pi_t = 1/2(\pi_{11} + \pi_{12} - \pi_{44})$.

Figure 1:
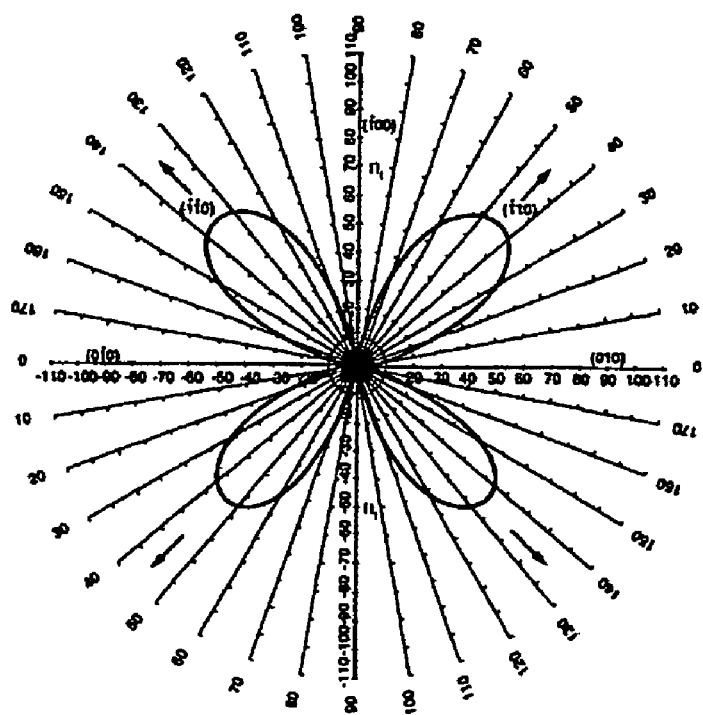
FIG. 1 shows the piezoresistive coefficients for $\pi_l$ and $\pi_t$ for p-type (A) and n-type (B) silicon. (At room temperature, in $10^{-11}$ Pa$^{-1}$).
Figure 1:
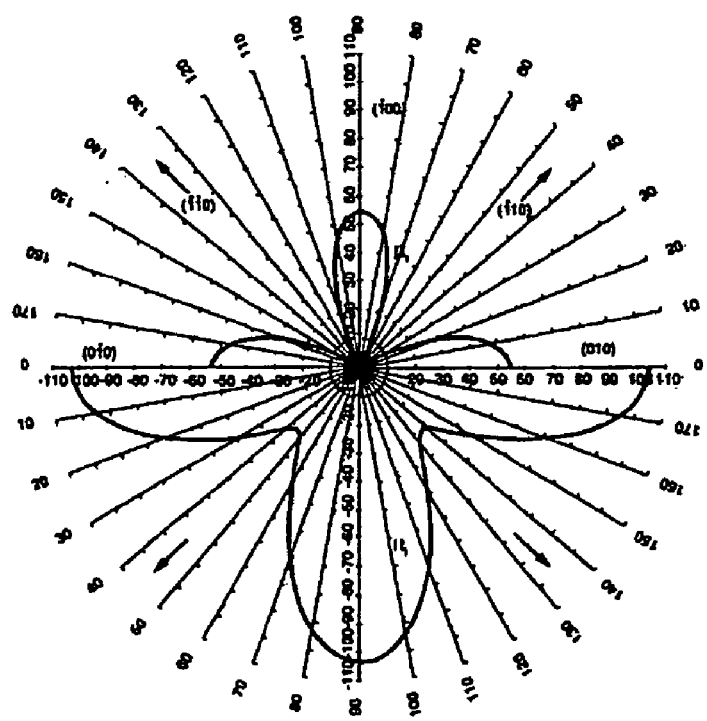

FIG. 1 shows the piezoresistive coefficients for $\pi_l$ and $\pi_t$ for p-type (A) and n-type (B) silicon. It is seen that the n-type piezoresistive coefficients are much more non-symmetrical than the p-type coefficients.

When a cantilever with integrated piezoresistor is used as a longitudinally deflection sensor only, the piezoresistor is placed such that only the longitudinal stress is picked up. Since the cantilevers are usually released by a wet etch, such as KOH, the cantilever may e.g. be aligned to the substrate such that a good clamping is obtained. Usually, the wet etch is anisotropically and etches the <111> direction much slower than the other directions. Since the intersection of the {111} plane and the {100} plane are lying along the <110> orientations, it has been found desired to align the cantilever in the <110> direction in order to release it with a good clamping.

According to the invention it has been found that the surface stress generated on a sensor unit comprising a capture surface, introduces a constant curvature or stretch or contraction at the areas where the surface stress is applied and no bending at places the surface stress is not applied. In areas adjacent a clamping line the bending in the clamping line direction (often also the transversal direction) direction may be limited. The constant curvature has shown to be obtained for both the transversal and the longitudinal direction. The situation can be visualised by placing the cantilever on a sphere. Since the surface stress changed is observed as a relative change in the resistance it has been found that both the transverse and longitudinal stress has to be considered, and furthermore, it has been found that they can be considered equally, irrespectively of the width and length of the piezoresistive material, when the cantilever is not subjected to other forces, such as a resistive force generated due to clamping. It has thus been found that an optimal signal or signal/noise ratio is obtained when the piezoresistive element is arranged so that the numerically value of the sum of the longitudinal piezoresistive coefficient $\pi_l$ and the transverse piezoresistive coefficient $\pi_t$ is at least (in $10^{-11}$ Pa$^{-1}$) 10×P, such as 20×P, such as 30×P, such as 40×P, wherein P is the piezoresistance factor.

Example 1

A simulation of the surface stress sensitivity for a cantilever with the following dimensions and as shown in FIG. 4, and with the piezoresistor placed in the <110> direction has been performed. In FIG. 4 the cantilever is seen in a sectional side view. The cantilever has a length of about 120 μm and a width of about 50 μm.

| Cantilever Dimensions | Thickness [nm] | Young's modulus [GPa] | Pre-stress [MPa] |
|---|---|---|---|
| Au | 30 | 80 | 40 |
| SiN | 45 | 200 | 85 |
| Si | 150 | 180 | 20 |
| SiO2 | 100 | 70 | −290 |
| SiN | 145 | 200 | 75 |

The single crystalline silicon piezoresistor was simulated with respectively, a p-type and an n-type resistor. The result is:

p-type $$\frac{\Delta R}{R} \bigg/ \sigma_s = 2.97 \cdot 10^{-4} (N/m)^{-1}$$

n-type $$\frac{\Delta R}{R} \bigg/ \sigma_s = -2.83 \cdot 10^{-3} (N/m)^{-1}$$

As seen from the simulation the sensitivity for an n-type single crystalline silicon piezoresistor used for surface stress sensitivity is almost a factor of 10 more sensitive than a p-type single crystalline silicon piezoresistor.

Example 2

In order to exemplify the increase of sensitivity by using an n-type piezoresistive cantilever as a surface stress sensor instead of a p-type piezoresistive cantilever, an experiment that changes the surface stress in a controlled manner is performed.

An example of such an experiment is measuring the change in surface stress when the molecule Mercaptohexanol is immobilized to a gold layer on the topside of a cantilever surface. The immobilization of Mercaptohexanol is performed due to the binding between the —SH group in Mercaptohexanol and the gold layer. The immobilization of Mercaptohexanol is finalized when a complete monolayer is formed on the gold surface. Since the surface stress of the cantilever is changed during this procedure, this can be monitored as a change in signal from the piezoresistive cantilever. When the monolayer has been formed the signal will become constant. The amplitude of the signal is then defined as difference between the signal before the introduction of Mercaptohexanol and the signal from the piezoresistor after the Mercaptohexanol monolayer is formed on the cantilever gold.

Figure 2:
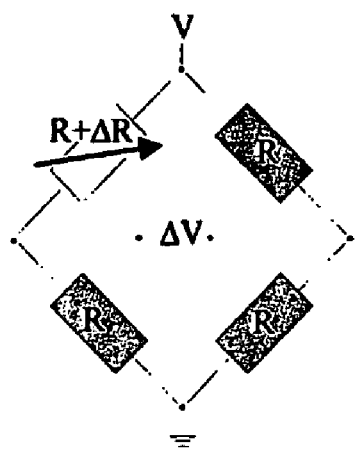
FIG. 2 shows a Wheatstone bridge for converting the relative change in resistance from the measurement cantilever into a change in voltage.

The experiment consists of observing the amplitude of two almost identical piezoresistive cantilevers, wherein the cantilevers differs in that one of the piezoresistive cantilevers has incorporated an n-type piezoresistor while the other has a p-type piezoresistor. In this example the piezoresistors is placed in the <110> direction of the silicon crystal and P=1 for both n-type and p-type. The piezoresistors are inserted in a Wheatstone bridge as seen in FIG. 2. The change in output voltage from the Wheatstone bridge is given:

$$\Delta V = \frac{1}{4} \frac{\Delta R}{R} \sigma_s \cdot V$$

Where $\Delta V$ is the output voltage and V is the input voltage, $\sigma_s$ is the surface stress and $\Delta R/R$ is the relative change of resistance of the piezoresistor. Since the relative change in resistance is given by:

$$\frac{\Delta R}{R} = \pi_l \cdot \sigma_l + \pi_t \cdot \sigma_t$$

Where $\pi_l$ and $\pi_t$ are the piezoresistive coefficients in the longitudinal and transversal direction, respectively. $\sigma_l$ and $\sigma_t$ are the stress in the piezoresistive layer. It can be assumed that $\sigma_l = \sigma_t = \sigma$ and $\sigma_s \propto \sigma$.

Using the above considerations together with the piezoresistive coefficients in the table 1, the output voltage for a p-type piezoresistive cantilever can be written as:

$$\Delta V_{p-type} \propto (\pi_l + \pi_t) \sigma_s \cdot V = 6 \cdot \sigma_s \cdot V$$

and for an n-type piezoresistor:

$$\Delta V_{n-type} \propto (\pi_l + \pi_t) \sigma_s \cdot V = -49 \cdot \sigma_s \cdot V$$

As it is seen from the two equations, there is a factor of about 8 in difference in sensitivity in favour of n-type piezoresistive cantilever, and the change in output voltage has opposite signs for the same surface stress.

In the experiment, the cantilevers are inserted in a micro liquid handling system as described in WO 0066266. The V=2.5 V is applied to the Wheatstone bridge (input voltage) and the signal from the Wheatstone bridge is monitored by a voltmeter. First, water is pumped through the system in order to stabilize the system. Hereafter, 1 mM Mercaptohexanol is introduced in the micro liquid handling system and the signal starts to change. The graph in FIG. 3 is an example of such an experiment. It can be seen that the signal from the n-type piezoresistive cantilever has a signal, which is about 8 times larger, and with opposite sign compared to the change in signal from the p-type piezoresistive cantilever.

Example 3

A cantilever as shown in FIG. 4 was provided. The gold was applied in the form of a film. During to the application of the gold film, the gold film was stretched in all directions, so that cantilever surface after the release of the gold layer was subjected to a stress. The stress of the surface was determined by finite element simulation. In the cantilever surface shown in FIG. 5 the stress is indicated by the white/grey/black colour. The darker the colour the higher is the stress that is measured. In areas 52 adjacent the clamping line 51 the bending in the clamping line direction is limited and accordingly the level of stress measured is less than longer away 53 from the clamping line. The rule of thumb is that the stress in both the transverse and longitudianal direction can be considered un-effected of the clamping when the distance X from the clamping is about $X > 0.25 \times W$ where W is the width of the cantilever.

The invention claimed is:

1. A sensor comprising at least one sensor unit shaped as a cantilever, said sensor unit comprises a capture surface, and a piezoresistive element with a pair of wires for applying an electrical field over the piezoresistive element, the distance between the wires along the piezoresistive element being defined as the length of the piezoresistive element, the piezoresistive element has a longitudinal direction and a transverse direction along the length of the piezoresistive element when an electrical field is applied over the piezoresistive element and the piezoresistive element is subjected to a stress, the longitudinal direction is defined as a direction which is one of the axis x, y or z of a coordinate system and wherein there is a stress component and a current component, the transverse direction is perpendicular to said longitudinal direction, said piezoresistive element being of an anisotropic material, and being arranged so that the numerical value of the sum of the longitudinal piezoresistive coefficient $\pi_l$ and the transverse piezoresistive coefficient $\pi_t$ along at least 25% of the length, of the piezoresistive element being at least $10^{-10} Pa^{-1} \times P$, wherein P is the piezoresistance factor, and wherein the piezoresistive coefficients $\pi_l$ and $\pi_t$ are determined as components in the coordinate system used to determine the longitudinal direction.

2. A sensor according to claim 1 wherein the piezoresistive element being of doped single crystalline silicon.

3. A sensor according to claim 1 wherein the sensor unit comprises a single crystalline silicon piezoresistive element encapsulated in a single crystalline silicon electrical shield.

4. A sensor according to claim 1 wherein the piezoresistive element is encapsulated in a shield of a non-conducting material selected from the group consisting of nitrides, non-conducting polymers, metal oxides, ceramics, diamond films, silicon carbide, tantalum oxide, silicon, glass, mixtures and combinations thereof.

5. A sensor according to claim 1 wherein said sensor unit is shaped as a cantilever extending in a length and linked in both of its endings to form a cantilevered bridge.

6. A sensor according to claim 1 wherein the sensor unit has a thickness in the interval of 0.05 μm to 5 μm.

7. A sensor according to claim 1 wherein the piezoresistive element has a thickness in the interval of 10 nm to 500 nm.

8. A sensor according to claim 1 wherein the piezoresistive element has a shape selected from the group consisting of U shaped, latter shaped, meander shaped and V shaped.

9. A sensor according to claim 1 wherein the piezoresistive element is n-type single crystalline silicon.

10. A sensor according to claim 9 wherein said n-type silicon piezoresistive element being orientated along the <110> direction of silicon.

11. A sensor according to claim 9 wherein said n-type silicon piezoresistive element being orientated along the <100> direction of silicon.

12. A sensor according to claim 1 wherein the piezoresistive element being of single crystalline silicon doped with one or more of the ions selected from the group consisting of boron ion, phosphorous ion and arsenic ion.

13. A sensor according to claim 1 wherein the piezoresistive element being of single crystalline silicon doped with at least $10^{16}$ ions/cm$^3$.

14. A sensor according to claim 1 wherein the piezoresistive element being of single crystalline silicon doped with maximum of $10^{21}$ ions/cm$^3$.

15. A sensor according to claim 1, wherein the sensor unit comprises two major surfaces, and at least a part of one or both of the major surfaces constitutes the capture surface, and the piezoresistive element has a neutral plan distance of maximum 50 nm, wherein the neutral plan distance is measured as the shortest distance between the middle plan of the piezoresistive element, defined as the middle plan through the piezoresistive element which is parallel to the neutral plan, and the neutral plan, wherein the neutral plan is defined as the plan along which the sum of the compressive and tensile stress acting on the piezoresistive element is as close to zero as possible.

16. A sensor according to claim 1, wherein the sensor unit comprises two major surfaces, which major surfaces partly or totally constitute a capture surface.

17. A sensor according to claim 1 wherein said sensor comprises one or more fluid chambers, said one or more sensor units partly or totally protrudes into said fluid chamber(s) so that a fluid applied in the chamber is capable of coming into contact with at least part of the surface of the sensor unit(s).

18. A sensor according to claim 1 wherein said fluid chamber or chambers is/are in the form of interaction chamber(s), preferably comprising a channel for feeding a fluid into the interaction chamber(s).

19. A sensor according to claim 1 wherein said sensor is adapted for use in detection of a substance in a liquid.

20. A sensor according to claim 4 wherein the piezoresistive element is encapsulated in a shield of nitrides selected from the group consisting of silicon nitride and tantalum nitride.

21. A sensor according to claim 4 wherein the piezoresistive element is encapsulated in a shield of the non-conducting polymer octafunctional epoxidized novalac.

22. A sensor according to claim 13 wherein the piezoresistive element being of single crystalline silicon doped with at least $10^{17}$ ions/cm$^3$.

23. A sensor according to claim 13 wherein the piezoresistive element being of single crystalline silicon doped with at least $10^{18}$ ions/cm$^3$.

24. A sensor according to claim 14 wherein the piezoresistive element being of single crystalline silicon doped with maximum $10^{20}$ ions/cm$^3$.

25. A sensor according to claim 14 wherein the piezoresistive element being of single crystalline silicon doped with maximum $10^{19}$ ions/cm$^3$.

26. A sensor according to claim 15, wherein the piezoresistive element has a neutral plan distance of maximum 400 nm.

27. A sensor according to claim 15, wherein the piezoresistive element has a neutral plan distance of maximum 3 μm.

* * * * *